United States Patent

Huber et al.

[11] Patent Number: 4,649,167
[45] Date of Patent: Mar. 10, 1987

[54] SULFONE-CONTAINING HINDERED AMINES

[75] Inventors: L. K. Huber, Wayne; J. L. Reilly, Landsdale, both of Pa.

[73] Assignee: Pennwalt Corporation, Philadelphia, Pa.

[21] Appl. No.: 799,532

[22] Filed: Nov. 14, 1985

[51] Int. Cl.[4] ...................... C08K 5/34; C07D 403/12; C07D 403/14
[52] U.S. Cl. ...................................... 524/99; 524/102; 524/103; 546/16; 546/188; 546/216; 546/221; 546/242; 546/261; 546/290; 546/300; 546/301
[58] Field of Search .................. 546/16, 188, 216, 221, 546/242, 261, 290, 300, 301; 524/102, 103, 99

[56] References Cited

U.S. PATENT DOCUMENTS 3,334,104 8/1967 Houlihan ........................ 546/188

Primary Examiner—Robert T. Bond

[57] ABSTRACT

Compounds having the formula

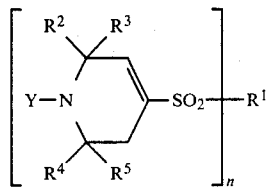

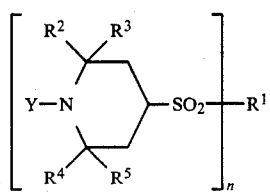

where $R^1$, $R^2$, $R^3$, $R^4$, and $R^5$ are independently selected from hydrocarbons, n is an integer of 1 to 15, and Y is H, OH, O, R where R is a hydrocarbon are useful as stabilizers for polymers against the detrimental effects produced by exposure to actinic radiation, such as visible or ultraviolet light rays.

14 Claims, No Drawings

SULFONE-CONTAINING HINDERED AMINES

BACKGROUND OF THE INVENTION

The present invention relates to novel piperidinyl sulfone derivatives containing a 2,2,6,6-tetramethylpiperidinyl-4-sulfonyl group which derivatives are useful for preventing ultraviolet light induced degradation of polymers.

Polyolefin resins, such as polyethylene and polypropylene, have long been used in the manufacture of foils, films, fibers, and molded articles. Because of their excellent structural properties, e.g., tensile strength, dimensional stability, etc., the manufactured materials have been extensively used in the construction trades. When used outdoors, however, these materials are continuously exposed to sunlight and UV radiation, which causes severe deterioration of the polyolefin resin, as evidenced by surface cracking, loss of tensile strength and discoloration.

Sterically hindered amines such as the tetramethyl piperidine type are known to stabilize polymers, especially polyolefins such as polypropylene and polyethylene, against degradation caused by UV radiation. Generally speaking, however, it is extremely difficult to predict the degree or extent to which a given hindered amine will protect polyolefins from UV light, since their performance depends upon a number of factors. Some otherwise useful hindered amines have a tendency to exude from polyolefin resins after incorporation, or decompose or evaporate during processing or thereafter, thus, leaving the resin inadequately protected against photodegradation. In addition, some of these hindered amines are also relatively soluble in water and organic solvents and, therefore, can be readily removed from the plastic matrix.

For the above reasons the prior art hindered amine stabilizers are not completely satisfactory and substantial research in this area is continuing. In recent years there have been repeated descriptions in patents (e.g., U.S. Pat. Nos. 4,435,555; 4,366,277; 4,340,534; 4,110,305; 4,107,139; 4,046,736; etc.) on improved hindered-amine stabilizers. A few of these compositions are sulfur-containing; however, none are commercially useful due to excessive odor and performance which is lower than that of similar non-sulfur containing compositions.

Randell, et al., U.S. Pat. No. 3,939,170, disclosed sulfides, sulfoxides, and sulfones having the formula:

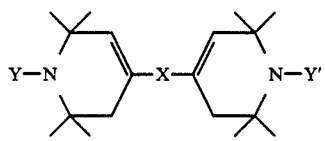

where X is S, SO, or SO$_2$ and Y and Y' are the same or different and each is H, OH, O or a straight- or branched-alkyl residue having from one to four carbon atoms, and salts thereof where Y and Y' are other than O. Mayer, et al., Ger. Offen. No. 2,513,607, disclosed dehydropiperidine sulfides and their salts having the formula:

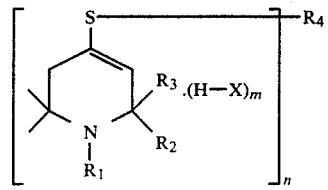

where R$_1$ can be H, OH, or a hydrocarbon group; R$_2$, R$_3$, and R$_4$ can be hydrocarbons and H—X can be phosphorous-, phosphoric-, an aliphatic sulfonic-, or phosphonic acid.

SUMMARY OF THE INVENTION

It has now been surprisingly discovered, in accordance with the present invention, that a certain class of sulfone-containing hindered amines when incorporated in a polyolefin resin, are highly effective as stabilizers against the detrimental effects produced by exposure to light. More particularly, the present invention is directed to novel sulfone-containing hindered amines of the formula (I) or (II) and their salts:

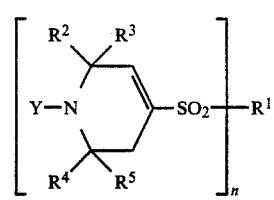

I

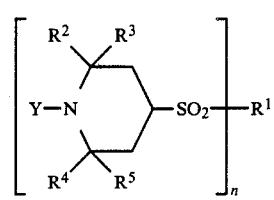

II wherein
R$^1$ is selected from the group of alkyl having 1 to 30 carbons, cycloalkyl and cycloalkenyl having 3 to 20 carbons, cycloalkylalkyl having 4 to 30 carbons, aryl having 6 to 30 carbons, and alkylaryl having 7 to 30 carbons, which radicals may optionally be substituted with substituents from the group of halogen, OH, OR, O$_2$CR, CO$_2$R, COR, CONH$_2$, CONR$_2$, CONHR, NH$_2$, NR$_2$, NHR, SR, SOR, SO$_2$R, SO$_2$NR$_2$, SO$_2$NH$_2$, SO$_2$NHR, or may contain as linking groups, —O—, —NH—, —NR—, —CO—, —CO$_2$—, —COHN—, —CONR—, —S—, —SO—, —SO$_2$—, —SO$_2$NH—, —SO$_2$NR—;

R is selected from the group of alkyl having 1 to 20 carbons, alkenyl having 2 to 20 carbons, cycloalkyl having 3 to 20 carbons, aryl having 6 to 20 carbons, or alkylaryl or arylalkyl having 7 to 20 carbons;

n is an integer of from 1 to 15;

R$^2$, R$^3$, R$^4$ and R$^5$ are the same or different and are selected from the group of alkyl having 1 to 10 carbons, alkenyl having 2 to 10 carbons, cycloalkyl having 3 to 10 carbons, aryl having 6 to 20 carbons or alkylaryl having 7 to 20 carbons, or R$^2$ and R$^3$, and R$^4$ and R$^5$ may be linked together to form a ring with 5 to 12 carbons; and Y is selected from H, OH, O, or a hydrocarbyl radical R wherein R is defined as above.

Preferred sulfone-containing hindered amines are those wherein $R^1$ is an alkyl, cycloalkyl, or cycloalkylkyl group having 5 to 15 carbon atoms; n is 1 to 5; $R^2$, $R^3$, $R^4$, and $R^5$ are methyl; and Y is selected from H, OH, O, or methyl.

Representative sulfone-containing hindered amine falling within the above formulas are:

1-(or2),3-(or 4)-bis(2,2,6,6-tetramethylpiperidinyl-4-sulfonyl)cyclooctane
1-(or 2),3-(or 4)-bis(3,4-dehydro-2,2,6,6-tetramethylpiperidinyl-4-sulfonyl)cyclooctane
1,5-(or 6)-bis(2,2,6,6-tetramethylpiperidinyl-4-sulfonyl)cyclooctane
1,5-(or 6)-bis(3,4-dehydro-2,2,6,6-tetramethylpiperidinyl-4-sulfonyl)cyclooctane
5-(or 6),9-(or 10)-bis(3,4-dehydro-2,2,6,6-tetramethylpiperidinyl-4-sulfonyl)cyclododecene
1,5-(or 6)bis(2,2,6,6-tetramethylpiperidinyl-4-sulfonyl)cyclododecane
bis[2-(2,2,6,6-tetramethylpiperidinyl-4-sulfonyl)ethyl]adipate
bis[2-(3,4-dehydro-2,2,6,6-tetramethylpiperidinyl-4-sulfonyl)ethyl]sebacate
bis[2-(2,2,6,6-tetramethylpiperidinyl-4-sulfonyl)ethyl]sebacate
beta(2,2,6,6-tetramethylpiperidinyl-4-sulfonyl)ethylbenzene 3-(3,4-dehydro-2,2,6,6-tetramethylpiperidinyl-4-sulfonyl)propionic acid neopentanetetrayl ester
3-(2,2,6,6-tetramethylpiperidinyl-4-sulfonyl)propionic acid neopentanetetrayl ester
(2,2,6,6-tetramethylpiperidinyl-4-sulfonyl)acetic acid neopentanetetrayl ester
(3,4-dehydro-2,2,6,6-tetramethylpiperidinyl-4-sulfonyl-)acetic acid neopentanetetrayl ester Some examples of the preferred sulfur-containing hindered amines include:

1,6-bis(2,2,6,6-tetramethylpiperidinyl-4-sulfonyl)hexane
1,6-bis(3,4-dehydro-2,2,6,6-tetramethylpiperidinyl-4-sulfonyl)hexane
beta(2,2,6,6-tetramethylpiperidinyl-4-sulfonyl)ethyl-3 and 4-(2,2,6,6-tetramethylpiperidinyl-4-sulfonyl)cyclohexane
beta(3,4-dehydro-2,2,6,6-tetramethylpiperidinyl-4-sulfonyl)ethyl-3 and 4-(3,4-dehydro-2,2,6,6-tetramethylpiperidinyl-4-sulfonyl)cyclohexane
2,9-bis(2,2,6,6-tetramethylpiperidinyl-4-sulfonyl)-p-menthane
2,9-bis(3,4-dehydro-2,2,6,6-tetramethylpiperidinyl-4-sulfonyl)-p-menthane
1,4-(or 5),8-(or 9)-tris(2,2,6,6-tetramethylpiperidinyl-4-sulfonyl)cyclododecane
1,4-(or 5),8-(or 9)-tris(3,4-dehydro-2,2,6,6-tetramethylpiperidinyl-4-sulfonyl)cyclododecane
1,5-(or 6),9-(or 10)-tris(2,2,6,6-tetramethylpiperidinyl-4-sulfonyl)cyclododecane
1,5-(or 6),9-(or 10)-tris(3,4-dehydro-2,2,6,6-tetramethylpiperidinyl-4-sulfonyl)cyclododecane
3,3'-bis(2,2,6,6-tetramethylpiperidinyl-4-sulfonyl)propyl ether
3,3'-bis(3,4-dehydro-2,2,6,6-tetramethylpiperidinyl-4-sulfonyl)propyl ether The sulfone-containing hindered amines of this invention have excellent stabilizer activity and compatibility with polyolefins (e.g., polyethylene and polypropylene), low volatility and low extractability from polymers by laundering or dry cleaning solvents.

The sulfone-containing hindered amines of this invention can be conveniently prepared. The reaction of equal-molar proportions of a mercaptan and a 4-oxopiperidine gives the corresponding vinyl sulfide, shown below.

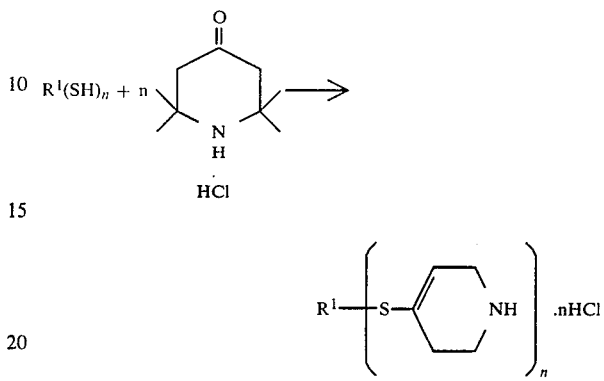

These vinyl sulfides can then be oxidized to the corresponding sulfones using the conventional oxidizing agents such as hydrogen peroxide, hypochlorite ion, peracetic acid, or nitric acid. The reduction of these vinyl sulfides or sulfones gives the corresponding saturated composition.

The compositions of the present invention are effective for stabilizing a wide variety of polymers, especially polyolefin resins, against deterioration caused by exposure to actinic radiation. As used in this description and in the appended claims, the term "polyolefin" is intended to include any normally solid polymer derived from the polymerization of a mono-α-olefinic aliphatic and aryl-substituted aliphatic hydrocarbon having 2 through 20 carbons, and copolymers thereof. This definition is intended also to include polymers of diolefins, as well as olefin/diolefin copolymers. The aforesaid polymeric materials may contain vinyl monomers or substituted vinyl monomers, such as acrylonitrile, styrene, vinyl halide, vinylidene halide, vinyl acetate, and the like. Specific examples of the polymers and copolymers which can be rendered stable to actinic radiation in accordance with the present invention are polyethylene, polypropylene, polyisobutylene, poly-2-methylpentene, poly-4-methylpentene, poly-2-methylbutene, polyisoprene, polybutadiene, ethylene-mono-olefin copolymers wherein the mono-olefin has 3 to 20 carbon atoms, propylene-isobutylene copolymers, styrene-butadiene copolymers, styrene-isoprene copolymers, ethylene-vinyl acetate copolymers, vinylidene fluoride-ethylene copolymers, and acrylonitrile-butadienestyrene terpolymers.

The stabilizer composition of the present invention can be used over a range of from about 0.05 to about 5.0 parts by weight per 100 parts of resin. The preferred range is from about 0.05 to about 3.0 parts by weight per 100 parts of resin.

The compositions of this invention can be incorporated into the polymer resin by any of several well known procedures which provide for uniform distribution in the polymer, such as milling on heated rolls. It has been found effective to mix the stabilizer into the resin by milling the materials on a two-roll mill at 200° C. The polyolefin resin containing the above light stabilizer compositions can then be extruded, injection molded, blow molded, or compression molded into useful articles, such as film, fibers, pipes, or bottles.

These novel light stabilizer compositions can be used as the sole stabilizer or in combination with other conventional light stabilizers such as benzophenones, e.g., 2-hydroxy-4noctoxybenzophenone; aromatic acid esters, e.g., 2,4-di-t-butylphenyl-3,5-di-t-butyl-4-hydroxybenzoate; benzotriazoles, e.g., 2(2-hydroxy-5-methylphenyl)benzotriazole; and nickel compounds, e.g., nickel dibutyl dithiocarbamate. Primary and secondary antioxidants such as hindered phenols, e.g., pentaerythritol tetrakis(3,5-di-t-butyl-4-hydroxyhydrocinnamate); phosphites, e.g., distearyl pentaerythritol diphosphite; organic amines, e.g., N,N'-diphenyl-p-phenylenediamine; and organic sulfides, e.g., distearyl thiodipropionate can be used in combination with the novel stabilizer compositions of this invention.

Other conventional polymer addivites such as processing aids, antiblocking and slip agents, biocides, flame retardants, smoke suppressants, coupling and wetting agents, pigments (titanium dioxide, carbon black, and many others), and fillers and/or reinforcements (mica, clay, talc, organic fibers, carbon/graphite fibers, and many others) can also be used in combination with the stabilizers of this invention.

The following examples further describe the manner and process of making and using the present invention and set forth the best mode contemplated for carrying out the invention but are not to be construed as limiting the invention.

In the following examples, all amounts given in parts are parts by weight, unless otherwise indicated. Experiments A, B, C, D, etc. are preparations of precussor compounds (or intermediates) used to prepare novel compounds of the present invention.

EXPERIMENT A

Preparation of
1,6-Bis(3,4-dehydro-2,2,6,6-tetramethylpiperidinyl-4-thio)hexane

A stirred mixture of 50.0 g (0.261 moles) of 2,2,6,6-tetramethyl-4-piperdone hydrochloride, 19.6 g (0.130 moles) of 1,6-hexanedithiol, 27.6 g (0.287 moles) of methane sulfonic acid, and 160 ml of xylene were brought to reflux under a blanket of nitrogen in a three-necked flask equipped with a Dean-Stark trap for removal of water from the reaction mixture. After six hours of reflux, the mixture was cooled slightly and the xylene was decanted from the viscous bottom layer. An additional 100 ml of xylene were added and the mixture was heated to reflux, cooled, and the xylene decanted. The viscous residue was dissolved in 100 ml of ethanol, and 10.5 g of sodium hydroxide dissolved in 100 ml of ethanol were added. The mixture was then cooled and the salt precipitate was filtered and washed with 100 ml of hexane. The ethanol/hexane solution was evaporated under vacuum yielding 42 g of an off-white solid which was recrystallized from hexane, m.p. 78°–81° C.; IR (mull) 1627 (C=C) cm$^{-1}$.

EXAMPLE 1

Preparation of
1,6-Bis(3,4-dehydro-2,2,6,6-tetramethylpiperdinyl-4-sulfonyl)hexane To a stirred mixture of 18.8 g (0.0443 moles) of the product from Experiment A, 0.9 g of sodium tungstate and 0.9 g of tetraethyl ammonium chloride in 160 ml of methanol, 73.7 g (0.650 moles) of 30% hydrogen peroxide were added over a one hour period. During this addition the temperature rose from 20° C. to 40° C. The solution was stirred at room temperature for 24 hours, filtered and dried yielding 19.0 g of an off-white powder. Recrystallization from dioxane yielded 18.0 g of a white powder, m.p. 212°–214.5° C.

Anal. Calcd. for $C_{24}H_{44}N_2O_4S_2$: C, 58.98; H, 9.07; N, 5.73; O, 13.09; S, 13.12. Found: C, 58.5; H, 8.94; N, 5.75; S, 13.7.

EXAMPLE 2

Preparation of
1,6-Bis(2,2,6,6-tetramethylpiperidinyl-4-sulfonyl)hexane

To a stirred mixture of 4 g of the product of Example 1 in 50 ml of tetrahydrofurane, 4 g of lithium aluminum hydride were added. After eight hours of reflux, the mixture was cooled in an ice bath and 100 ml of ether were added and the reaction was quenched slowly with 4 ml of water, followed by 4 ml of 10% sodium hydroxide and finally with 12 ml of water. The precipitate was filtered and washed with 100 ml of tetrahydrofurane. The solvent was removed yielding 3.6 g of a white solid, m.p. 185°–188° C.

Anal. Calcd. for $C_{24}H_{48}N_2O_4S_2$: C, 58.50; H, 9.82; N, 5.68; O, 12.99; S, 13.01. Found: C, 58.5; H, 9.81; N, 5.36; S, 12.9.

EXPERIMENT B

Preparation of
Beta(3,4-dehydro-2,2,6,6-tetramethylpiperidinyl-4-thio)ethyl-3 and
4-(3,4,-dehydro-2,2,6,6-tetramethylpiperidinyl-4-thio)cyclohexane The procedure used was the same as described in Experiment A. A stirred mixture of 25 g (0.130 mole) of tetramethyl-4-piperidone hydrochloride, 11.5 g (0.0652 mole) of beta-mercaptoethyl-3 and 4-mercaptocyclohexane (prepared as a mixture of isomers and not separated), 13.8 g (0.144 mole) of methane sulfonic acid, and 100 ml of xylene were refluxed for six hours in a flask equipped with a Dean-Stark trap for removal of water. Normal workup yielded 21.5 g of a light yellow oil, IR (neat) 1621 (S—C=C) cm$^{-1}$.

EXAMPLE 3

Preparation of
Beta(1-oxyl-3,4-dehydro-2,2,6,6-tetramethylpiperidinyl-4-sulfonyl)ethyl-3 and
4-(1-oxyl-3,4-dehydro-2,2,6,6-tetramethylpiperidinyl-4-sulfonyl)cyclohexane The procedure used was the same as in Example 1. To a stirred mixture of 4.5 g (0.0100 mole) of the product of Experiment B, 0.2 g of sodium tungstate, and 0.2 g of tetraethyl ammonium chloride in 40 ml of methanol, 16.0 g (0.141 mole) of 30% hydrogen peroxide were added. The solution was stirred at room temperature for 24 hours, filtered and dried yielding 3 g of a pink powder, m.p. 206°–209° C.

Anal. Calcd. for $C_{26}H_{44}N_2O_6S_2$: C, 57.32; H, 8.14; N, 5.14; O, 17.62; S, 11.77. Found: C, 57.2; H, 7.68; N, 4.66; S, 12.0.

EXAMPLE 4

Preparation of Beta(3,4-dehydro-2,2,6,6-tetramethylpiperidinyl-4-sulfonyl)ethyl-3 and 4-(3,4-dehydro-2,2,6,6-tetramethylpiperidinyl-4-sulfonyl)cyclohexane To a stirred solution of 24.0 g (0.0535 mole) of the product of Experiment B in 200 ml of acetic acid, 42.7 g (0.225 mole) of 40% peracetic acid were added dropwise keeping the temperature under 30° C. The reaction mixture was stirred at room temperature for one hour after which the solvent was removed under vacuum at 60° C. The residue was dissolved in 200 ml of water and extracted with 100 ml of chloroform. The aqueous layer was basified with sodium hydroxide to a pH of 9 and extracted three times with 75 ml of methylene chloride. Removal of the solvent under vacuum yielded 19.0 g of an off-white solid, which was recrystallized from toluene, m.p. 217°–224° C.

Anal. Calcd. for $C_{26}H_{46}N_2O_4S_2$: C, 60.66; H, 9.01; N, 5.44; O, 12.43; S, 12.46. Found: C, 60.8; H, 9.02; N, 5.16; S, 12.7.

EXAMPLE 5

Preparation of Beta(2,2,6,6-tetramethylpiperidinyl-4-sulfonyl)ethyl-3 and 4-(2,2,6,6-tetramethylpiperidinyl-4-sulfonyl)cyclohexane To a stirred mixture of 4 g of the product of Example 4 in 50 ml of tetrahydrofurane, 4 g of lithium aluminum hydride were added. After eight hours of reflux, the mixture was cooled in an ice bath and 100 ml of ether were added and the reaction was quenched slowly with 4 ml of water followed by 4 ml of 10% sodium hydroxide and finally with 12 ml of water. The precipitate was filtered and washed with 100 ml of tetrahydrofurane. The solvent was removed yielding 3.5 g of an off-white powder, m.p. 215°–223° C.

Anal. Calcd. for $C_{26}H_{50}N_2O_4S_2$: C, 60.19; H, 9.71; N, 5.40; O, 12.33; S, 12.36. Found: C, 59.9; H, 9.96; N, 5.19; S, 12.9.

EXPERIMENT C

Preparation of 2,9-Bis(3,4-dehydro-2,2,6,6-tetramethylpiperidinyl-4-thio)-p-menthane The procedure used was the same as in Experiment A. A stirred mixture of 25 g (0.130 mole) of tetramethyl-4-piperidone hydrochloride, 13.3 g (0.0652 mole) of 2,9-dimercapto-p-menthane, 13.8 g (0.144 mole) of methane sulfonic acid, and 100 ml of xylene were refluxed for six hours in a flask equipped with a Dean-Stark trap for removal of water from the reaction mixture. Normal workup yielded 24.5 g of a light yellow oil, IR (neat) 1627 (S—C=C) cm$^{-1}$.

EXAMPLE 6

Preparation of 2,9-Bis(1-oxyl-3,4-dehydro-2,2,6,6-tetramethyl-piperidinyl-4-sulfonyl)-p-menthane The procedure used was the same as in Example 1. To a stirred mixture of 4.8 g (0.010 mole) of the product of Experiment C, 0.2 g of tetraethyl ammonium chloride, and 0.2 g of sodium tungstate in 40 ml of methanol, 17.5 g (0.154 mole) of 30% hydrogen peroxide were added. The solution was stirred at room temperature for 24 hours, filtered and dried yielding 1.8 g of a pink powder, m.p. 140°–154° C.

Anal. Calcd. for $C_{28}H_{48}N_2O_6S_2$: C, 58.71; H, 8.45; N, 4.89; O, 16.76; S, 11.19. Found: C, 57.2; H, 7.7; N, 4.7; S, 12.0.

EXAMPLE 7

Preparation of 2,9-Bis(3,4-dehydro-2,2,6,6-tetramethylpiperidinyl-4-sulfonyl)-p-menthane The procedure used was the same as in Example 4. To a stirred mixture of 24.5 g (0.0514 mole) of the product of Experiment C in 200 ml of acetic acid, 41.0 g (0.216 mole) of 40% peracetic acid were added dropwise keeping the temperature under 30° C. The reaction mixture was stirred at room temperature for one hour and then normal workup yielded 9 g of a solid which was recrystallized from toluene, m.p. 169°–172° C.

Anal. Calcd. for $C_{28}H_{50}N_2O_4S_2$: C, 61.95; H, 9.28; N, 5.16 O, 11.79; S, 11.81. Found: C, 62.8; H, 9.46; N, 5.09; S, 10.8.

EXPERIMENT D

Preparation of 3,3'-Bis(3,4-dehydro-2,2,6,6-tetramethylpiperidinyl-4-thio)propyl ether The procedure used was the same as described in Experiment A. A stirred mixture of 25 g (0.130 mole) of tetramethyl-4-piperidone hydrochloride, 10.8 g (0.0652 mole) of 3,3'-dithiopropylether, 13.8 g (0.144 mole) of methane sulfonic acid, and 100 ml of xylene were refluxed for six hours in a flask equipped with a Dean-Stark trap for removal of water. Normal workup yielded 23.5 g of a light yellow oil, IR (neat) 1630 (S—C=C) cm$^{-1}$.

EXAMPLE 8

Preparation of 3,3'-Bis(1-oxyl-3,4-dehydro-2,2,6,6-tetramethyl-piperidinyl-4-sulfonyl)propyl ether The procedure used was the same as in Example 1. To a stirred mixture of 4.4 g (0.00621 mole) of the product of Experiment D, 0.2 g of sodium tungstate, 0.2 g of tetraethyl ammonium chloride in 40 ml of methanol, and 18 g (0.159 mole) of 30% hydrogen peroxide were added. The solution was stirred at room temperature for 48 hours, filtered, and dried yielding 2.4 g of a pink powder, m.p. 172°–174° C.

Anal Calcd. for $C_{24}H_{42}N_2O_7S_2$: C, 53.91; H, 7.92; N, 5.24; O, 20.94; S, 11.99. Found: C, 54.2; H, 7.93; N, 4.96; S, 12.1.

EXAMPLE 9

Preparation of 3,3'-Bis(3,4-dehydro-2,2,6,6-tetramethylpiperidinyl-4-sulfonyl)propyl ether The procedure used was the same as in Example 4. To a stirred mixture of 6.7 g (0.0152 mole) of the product of Experiment D in 50 ml of acetic acid, 12.2 g (0.0642 mole) of 40% peracetic acid were added dropwise keeping the temperature under 30° C. The reaction mixture was stirred at room temperature for one hour. Standard workup yielded 5.8 g of an off-white solid, m.p. 142°–145° C.

Anal. Calcd. for $C_{24}H_{44}N_2O_5S_2$: C, 57.11; H, 8.79; N, 5.55; O, 15.85; S, 12.70. Found: C, 56.7; H, 8.77; N, 4.70; S, 11.8.

EXPERIMENT E

Preparation of 1,4-(or 5), 8-(or 9)-Tris(3,4-dehydro-2,2,6,6-tetramethylpiperidinyl-4-thio)cyclododecane The procedure used was the same as described in Experiment A. A stirred mixture of 25 g (0.130 mole) of tetramethyl-4-piperidone hydrochloride, 11.5 g (0.0435 mole) of 1,4 (or 5), 8 (or 9) trimercaptocyclododecane (prepared as a mixture of isomers and not separated), 13.8 g (0.144 mole) of methane sulfonic acid, and 100 ml of xylene were refluxed for six hours in a flask equipped with a Dean-Stark trap for removal of water. Normal workup yielded 15.0 g of a tan viscous oil, IR (neat) 1635 (S—C=C) cm$^{-1}$.

EXAMPLE 10

Preparation of 1,4-(or 5), 8-(or 9)-Tris(1-oxyl-3,4-dehydro-2,2,6,6-tetramethylpiperidinyl-4-sulfonyl)cyclododecane The procedure used was the same as in Example 1. To a stirred mixture of 4.2 g (0.00621 mole) of the product of Experiment E, 0.2 g of sodium tungstate, and 0.2 g of tetraethyl ammonium chloride in 40 ml of methanol, and 13.8 g (0.122 mole) of 30% hydrogen peroxide were added. The solution was stirred at room temperature for 24 hours, filtered, and dried yielding 4,4 g of a pink powder, m.p. 208°–211° C.

Anal. Calcd. for $C_{39}H_{66}N_3O_9S_3$: C, 57.32; H, 8.14; N, 5.14; O, 17.62; S, 11.77. Found: C, 57.1; H, 8.23; N, 4.95; S, 11.9.

EXAMPLE 11

Preparation of 1,4-(or 5), 8-(or 9)-Tris(3,4-dehydro-2,2,6,6-tetramethylpiperidinyl-4-sulfonyl)cyclododecane The procedure used was the same as in Example 4. To a stirred mixture of 5.0 g (0.00739 mole) of the product of Experiment E in 50 ml of acetic acid, 8.9 g (0.0468 mole) of 40% peracetic acid were added dropwise keeping the temperature under 30° C. The reaction mixture was stirred at room temperature for one hour and then normal workup yielded 4.6 g of an off-white solid which was recrystallized from toluene, m.p. 190°–196° C.

Anal. Calcd. for $C_{39}H_{69}N_3O_6S_3$: C, 60.66; H, 9.01; N, 5.44; O, 12.43; S, 12.46. Found: C, 61.5; H, 9.1; N, 5.2; S, 11.6.

EXAMPLE 12

Preparation of 1,6-Bis(3,4-dehydro-2,2,6,6-tetramethylpiperidinyl-4-sulfinyl)hexane To a stirred ice cold mixture of 14.2 g (0.066 mole) of sodium metaperiodate in 100 ml of water plus 50 ml of methanol, 14.2 g (0.033 mole) of the product of Experiment A in 100 ml of methanol were added dropwise. After additional stirring for 8 hours at 5°–10° C., the resulting slurry was kept in ice overnight. The mixture was then filtered and the filtrate freed from solvent. The resulting crude product (13.8 g) was recrystallized from an isopropanol/hexane mixture, to yield a white solid, m.p. 139°–143° C.

Anal. Calcd. for $C_{24}H_{44}N_2O_2S_2$: C, 63.09; H, 9.71; N, 6.13; S, 14.05 Found: C, 63.3; H, 10.0; N, 6.4; S, 13.9

EXAMPLE 13

Preparation of Bis[2-(3,4-dehydro-2,2,6,6-tetramethylpiperidinyl-4-sulfonyl)ethyl]adipate A stirred mixture of 50 g (0.263 mole) of 2,2,6,6-tetramethyl-4-piperdone hydrochloride, 33.7 g (0.126 mole) of bis(2-mercaptoethyl)adipate, 27.6 g (0.287 mole) of methane sulfonic acid, and 160 ml of xylene are brought to reflux under a blanket of nitrogen in a three-necked flask equipped with a Dean-Stark trap for removal of water from the reaction mixture. After six hours of reflux, the mixture is cooled slightly and the xylene decanted from the viscous bottom layer. An additional 100 ml of xylene is added and the mixture is heated to reflux, cooled, and the xylene decanted. The viscous residue is dissolved in 100 ml of ethanol and 10.5 g of sodium hydroxide dissolved in 100 ml of ethanol is added. The mixture is then cooled and the salt precipitate is filtered and washed with 100 ml of hexanes. The ethanol/hexane solution is evaporated under vacuum yielding bis[2-(3,4-dehydro-2,2,6,6-tetramethylpiperidinyl-4-thio)ethyl]adipate (a precussor). This compound is then oxidized to the corresponding sulfone by stirring into 4.2 g of the compound (precussor) 0.2 g of sodium tungstate, 0.2 g of tetraethyl ammonium chloride in 40 ml of methanol, and 13.8 g of 30% hydrogen peroxide. The solution is stirred at room temperature for 24 hours, filtered, and dried.

EXAMPLE 14

Preparation of 3-(3,4-dehydro-2,2,6,6-tetramethylpiperidinyl-4-sulfonyl)propionic acid neopentanetetrayl ester A stirred mixture of 50 g (0.263 mole) of 2,2,6,6-tetramethyl-4-piperdone hydrochloride, 31.9 g (0.0653 mole) of pentaerythritol tetra(3-mercaptopropionate), 27.6 g (0.287 mole) of methane sulfonic acid, and 160 ml of xylene are brought to reflux under a blanket of nitrogen in a three-necked flask equipped with a Dean-Stark trap for removal of water from the reaction mixture. After six hours of reflux, the mixture is cooled slightly and the xylene is decanted from the viscous bottom layer. An additional 100 ml of xylene is added and the mixture is heated to reflux, cooled, and the xylene decanted. The viscous residue is dissolved in 100 ml of ethanol and 10.5 g of sodium hydroxide dissolved in 100 ml of ethanol is added. The mixture is then cooled and the salt precipitate is filtered and washed with 100 ml of hexane.The ethanol/hexane solution is evaporated under vacuum yielding 3-(3,4-dehydro-2,2,6,6-tetramethylpiperidinyl-4-thio)propionic acid neopentanetetrayl ester (a precussor). This precussor is then oxidized to the corresponding sulfone using the same procedure as used in Example 13.

EXAMPLES 15–27

Test specimens were made from 100 parts of polypropylene (Profax 6501, Hercules) 0.05 parts pentaerythritol tetrakis[3,5-di-t-butyl-4-hydroxyhydrocinnamate], 0.1 part calcium stearate, and the light stabilizers listed in Table I. A methylene chloride slurry of the ingredients was made and the solvent was removed under vacuum on a rotary evaporator. The resulting mixtures were extruded in a one-inch laboratory extruder (temperature profile: Zone 1=190° C., Zone 2=200° C., Zone 3=210° C.) through a six-inch sheet die (temperature 215° C.). The 2 mil film was taken up on a Univex Extruder Take Off with a roll temperature of 18° C.

Each film was cut into 0.5×5 inch test specimens which were exposed in an Atlas Model Ci35 Weather-Ometer at a black pane temperature of 63°±3° C. Periodically, several specimens were removed to determine the retention of the tensile strength. The test results are reported in Table I as the time required for the test specimens to reach 50% of the initial tensile strength. The results tabulated below show that the subject compounds are highly active as light stabilizers.

TABLE I

| Example No. | Parts | Stabilizer | Hours to failure |
|---|---|---|---|
| Control | | None | 400 |
| Comparative I | 0.30 | 2-hydroxy-4n-octoxybenzophenone | 800 |
| Comparative II | 0.15 | Bis(2,2,6,6-tetramethyl-4-piperidyl) sebacate | 850 |
| Comparative IIA | 0.30 | Bis(2,2,6,6-tetramethyl-4-piperidyl) sebacate | 1500 |
| Comparative III | 0.30 | Product of Experiment A | 800 |
| 15 | 0.30 | Product of Example 1 | 1600 |
| 16 | 0.15 | Product of Example 2 | 1250 |
| 17 | 0.30 | Product of Example 2 | 1700 |
| Comparative IV | 0.30 | Product of Experiment B | 800 |
| 18 | 0.30 | Product of Example 3 | 1000 |
| 19 | 0.30 | Product of Example 4 | 1400 |
| 20 | 0.15 | Product of Example 5 | 1200 |
| 21 | 0.30 | Product of Example 5 | 1500 |
| Comparative V | 0.30 | Product of Experiment C | 800 |
| 22 | 0.30 | Product of Example 6 | 900 |
| 23 | 0.30 | Product of Example 7 | 1100 |
| Comparative VI | 0.30 | Product of Experiment D | 800 |
| 24 | 0.30 | Product of Example 8 | 1000 |
| 25 | 0.30 | Product of Example 9 | 1200 |
| Comparative VII | 0.30 | Product of Experiment E | 800 |
| 26 | 0.30 | Product of Example 10 | 900 |
| 27 | 0.30 | Product of Example 11 | 1100 |

What is claimed:

1. A compound of the formula (I) or (II) and the salts thereof

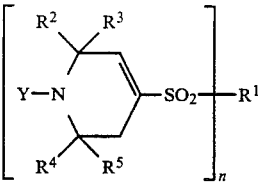

(I)

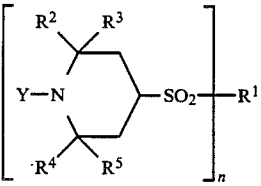

(II)

where
$R^1$ is selected from the group of alkyl having 1 to 30 carbons, cycloalkyl or cycloalkenyl having 3 to 20 carbons, cycloalkylalkyl having 4 to 30 carbons, aryl having 6 to 30 carbons and alkylaryl or arylalkyl having 7 to 30 carbons, which radicals may optionally be substituted with substituents from the group of halogen, OH, OR, $O_2CR$, $CO_2R$, $CONH_2$, CONR, CONHR, $NH_2$, $NR_2$, NHR, SR, SOR, $SO_2R$, $SO_2NR_2$, $SO_2NH_2$, $SO_2NHR$, or may contain as linking groups —O—, —NH—, —NR—, —CO—, —CO_2—, —CONH—, —CONR—, —S—, —SO—, —SO_2—, —CO_2NH—, and —SO_2NR—, R is selected from the group of alkyl having 1 to 20 carbons, alkenyl having 2 to 20 carbons, cycloalkyl or cycloalkenyl having 3 to 20 carbons, cycloalkylalkyl having 4 to 30 carbons, aryl having 6 to 20 carbons, and alkylaryl having 7 to 30 carbons, n is an integer of from 1 to 15, $R^2$, $R^3$, $R^4$ and $R^5$ are the same or different and are selected from the group of alkyl having 1 to 10 carbons, alkenyl having 2 to 10 carbons, cycloalkyl having 3 to 10 carbons, aryl having 6 to 20 carbons, or alkaryl having 7 to 20 carbons, or $R^2$ and $R^3$, and $R^4$ and $R^5$ may be linked together to form a ring with 5 to 12 carbons, and Y is selected from H, OH, O, or a hydrocarbyl radical R, wherein R is defined as above.

2. The compound of claim 1 wherein $R^2$, $R^3$, $R^4$ and $R^5$ are methyl.

3. The compound of claim 2 wherein Y is hydrogen.

4. The compound of claim 2 wherein Y is oxygen.

5. The compound of claim 3 wherein n is 2 or 3.

6. The compound of claim 5 wherein $R^1$ is selected from an alkyl of 5 to 15 carbons, a cycloalkyl or cycloalkenyl of 6 to 15 carbons, or a cycloalkylalkyl of 6 to 15 carbons.

7. The compound of claim 1 wherein the sulfone-containing hindered amine is selected from the group of 1,6-bis(2,2,6,6-tetramethylpiperidinyl-4-sulfonyl)hexane, 1,6-bis(3,4-dehydro-2,2,6,6-tetramethylpiperidinyl-4-sulfonyl)hexane, Beta(2,2,6,6-tetramethylpiperidinyl-4-sulfonyl)ethyl-3 and 4(2,2,6,6-tetramethylpiperidinyl-4-sulfonyl)cyclohexane, Beta(3,4-dehydro-2,2,6,6-tetramethylpiperidinyl-4-sulfonyl)ethyl-3 and 4(3,4-dehydro-2,2,6,6-tetramethylpiperidinyl-4-sulfonyl)cyclohexane, 2,9-bis(2,2,6,6-tetramethylpiperidinyl-4-sulfonyl)-p-menthane;

2,9-bis(3,4-dehydro-2,2,6,6-tetramethylpiperidinyl-4-sulfonyl)-p-menthane, 3,3'-bis(2,2,6,6-tetramethylpiperidinyl-4-sulfonyl)propyl ether, 3,3'-bis(3,4-dehydro-2,2,6,6-tetramethylpiperidinyl-4-sulfonyl)propyl ether, 1,4-(or 5), 8-(or 9)-tris(2,2,6,6-tetramethylpiperidinyl-4-sulfonyl)cyclododecane, and 1,4(or 5), 8-(or 9)-tris(3,4-dehydro-2,2,6,6-tetramethylpiperidinyl-4-sulfonyl)cyclododecane.

8. A composition comprising a polymer resin and an effective amount for stabilizing against degradation by ultraviolet light of the compound of claim 1.

9. The composition of claim 8 wherein the effective amount for stabilizing against degredation by ultraviolet light of the compound is from about 0.05 to about 5.0 parts by weight per 100 parts of polymer resin.

10. The composition of claim 9 wherein the polymer resin is selected from the group of polyethylene, polypropylene, polyisobutylene, poly-2-methylpentene, poly-4-methylpentene, poly-2-methylbutene, polyisoprene, polybutadiene, ethylene-mono-olefin copolymers wherein the mono-olefin has 3 to 20 carbon atoms, propylene-isobutylene copolymers, styrene-butadiene copolymers, styrene-isoprene copolymers, ethylene-vinyl acetate copolymers, vinylidene fluoride-ethylene copolymers, and acrylonitrile-butadiene-styrene terpolymers.

11. The composition of claim 10 wherein the polymer is selected from the group of polyethylene, polypropylene, or copolymers thereof.

12. A method for stabilizing polymer resin against degradation by UV-light which comprises incorporating in said polymer resin an effective amount of the compound of claim 1.

13. The method of claim 12 wherein the compound is incorporated in a polyolefin in an amount from about 0.05 to about 5.0 parts of the compound per 100 parts of polymer resin by weight.

14. The method of claim 13, wherein the compound is incorporated in a polymer resin in an amount from about 0.1 to about 3.0 parts of the compound per 100 parts of polyolefin, by weight.

* * * * *